United States Patent [19]
Huxel

[11] Patent Number: 5,972,022
[45] Date of Patent: *Oct. 26, 1999

[54] TISSUE ATTACHMENT DEVICE HAVING ELASTOMERIC SECTION

[75] Inventor: Shawn Thayer Huxel, Lakehurst, N.J.

[73] Assignee: Ethicon, Inc., Somerville, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/685,756

[22] Filed: Jul. 24, 1996

Related U.S. Application Data

[63] Continuation of application No. 08/312,351, Sep. 26, 1994, abandoned.

[51] Int. Cl.$^6$ .................................................. A61B 17/04
[52] U.S. Cl. ............................................. 606/215; 606/216
[58] Field of Search ................................. 606/215, 216, 606/220, 221, 230, 231, 228

[56] References Cited

U.S. PATENT DOCUMENTS

| | | | |
|---|---|---|---|
| 2,421,193 | 5/1947 | Gardner | 606/215 |
| 2,472,009 | 5/1949 | Gardner | 606/215 |
| 2,523,812 | 9/1950 | Carr | 606/221 |
| 3,103,218 | 9/1963 | Ajemian | 606/216 |
| 3,454,011 | 7/1969 | Wayner . | |
| 4,646,741 | 3/1987 | Smith | 606/220 |
| 4,994,073 | 2/1991 | Green | 606/220 |
| 5,236,438 | 8/1993 | Wilk | 606/216 |
| 5,468,253 | 11/1995 | Bezwada et al. | 606/220 |

FOREIGN PATENT DOCUMENTS

| | | | |
|---|---|---|---|
| 0854340 | 4/1940 | France | 606/215 |
| 0005163 | 3/1901 | United Kingdom | 606/221 |
| WO-A-90 14045 | 11/1990 | WIPO | A61B 17/00 |

*Primary Examiner*—Gary Jackson
*Attorney, Agent, or Firm*—Emil Richard Skula

[57] ABSTRACT

A surgical attachment device. The device has an elastomeric member which may be bioabsorbable. A tissue engagement means such as a hook is mounted to the elastomeric member. The tissue engagement means may also be bioabsorbable. The device provides tensioned fastening.

14 Claims, 4 Drawing Sheets

TISSUE ATTACHMENT DEVICE HAVING ELASTOMERIC SECTION

This is a continuation of U.S. application Ser. No. 08/312,351, filed Sep. 26, 1994, now abandoned.

TECHNICAL FIELD

The field of art to which this invention pertains is tissue fastening devices, in particular, tissue fastening devices for use in surgical procedures.

BACKGROUND OF THE INVENTION

Tissue attachment or fastening devices are well known in the medical and surgical arts. The devices may consist of staples, surgical tacks, sutures, and the like. The attachment devices may be made of conventional non-absorbable materials such as stainless steel and titanium. The devices may also be made from conventional non-absorbable polymeric materials. For many surgical procedures the fastening device of choice is one made from absorbable materials which are absorbed by the body over time.

Absorbable fastening devices have been found to be advantageous for several reasons. Absorbable fastening devices absorb as the patient heals; accordingly, it is not necessary to perform a second operation to remove the devices. In addition, after the fasteners absorb, they are not present to cause pain or other known complications. It is known that conventional fasteners made from non-absorbable materials are associated with residual pain and may migrate and cause a variety of complications.

Although conventional fastening devices are widely used and function adequately in surgical procedures, it is known that there are many surgical procedures where conventional tissue fastening devices or surgical fastening devices are deficient. For example, when affixing a surgical mesh or membrane to a tissue site as in the case of a repair of an inguinal hernia, it is often difficult to fasten the mesh so that it adequately conforms to the contours of the tissue or organ. Conventional tissue attachment devices tend to work adequately on flat tissue surfaces, however, it is difficult to achieve optimal tensioning when working with tissue or organs having contours. This is particularly evident when attempting to cover a tissue site or organ with a surgical mesh or other membrane. The conventional fasteners available to the surgeon may affix the mesh or membrane to the tissue or organ, however the surgeon must manipulate and support while fastening to properly tension the membrane or mesh. This is a difficult procedure and may possibly result in over-tensioning, tissue damage, or a poorly supported implant.

There is a need in this art for surgical or tissue fastening devices having the capability of providing tensioned fastening.

DISCLOSURE OF THE INVENTION

Therefore, it is an object of the present invention to provide a surgical or tissue fastener which provides tensioned fastening.

It is a further object of the present invention to provide a fastener capable of tensioned fastening which may be made of absorbable materials.

It is a further object of the present invention to provide a fastener which is easy and economical to manufacture.

It is still yet a further object of the present invention to provide the surgeon with a fastener which is easy for the surgeon to apply.

Still yet another object of the present invention is to provide a fastener which is readily used with contoured tissue and organs to provide tensioned fastening.

Accordingly, a surgical attachment device is disclosed. The device has an elastomeric member. At least one tissue engagement member is mounted to the elastomeric member. Preferably, the elastomeric member and the tissue engagement member are made from a bio-absorbable material. The device provides tensioned fastening. In a preferred embodiment, the tissue engagement member has a hook configuration and the hook has a distal piercing point with an optional barb.

Yet another aspect of the present invention is the combination of the above described fastening device and a surgical mesh or surgical membrane.

Still yet additional aspects of the present invention are methods of using both the above-described fastener and the combination.

These and other features and advantages of the invention will become more apparent from the following description and accompanying drawings.

DESCRIPTION OF PREFERRED EMBODIMENT

Figure 1:
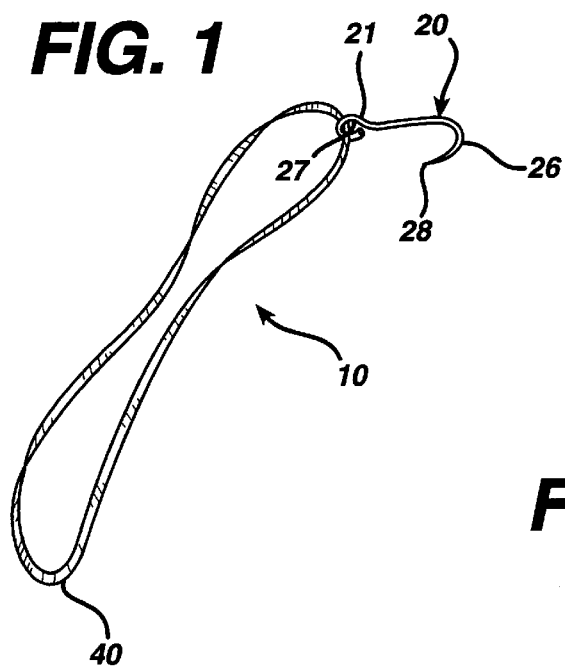
FIG. 1 is a perspective view of an embodiment of the fastening device of the present invention having a single hook mounted to an elastomeric member; the elastomeric member has an endless belt or band configuration.
Figure 10:
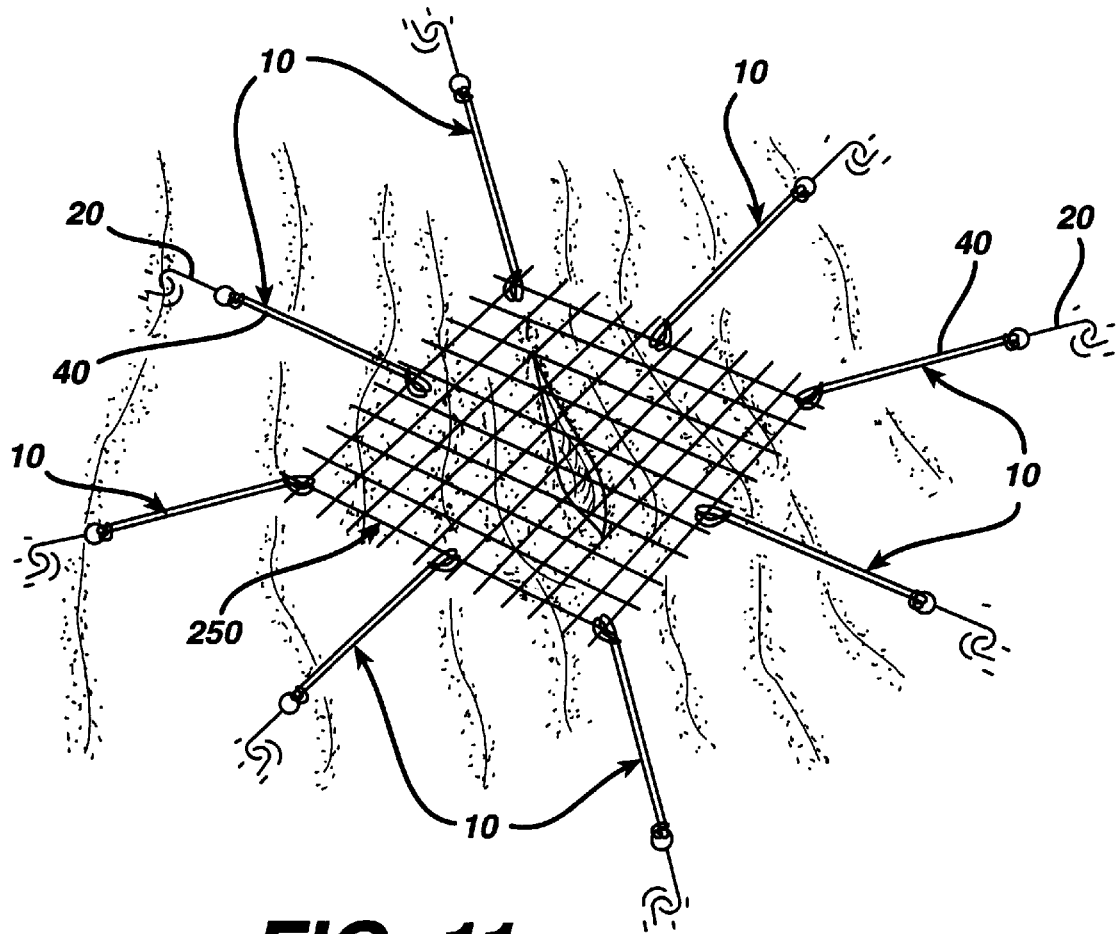
FIG. 10 is a perspective view of the attachment devices of the present invention used to secure a surgical mesh to a tissue site surrounding an inguinal hernia.
Figure 11:
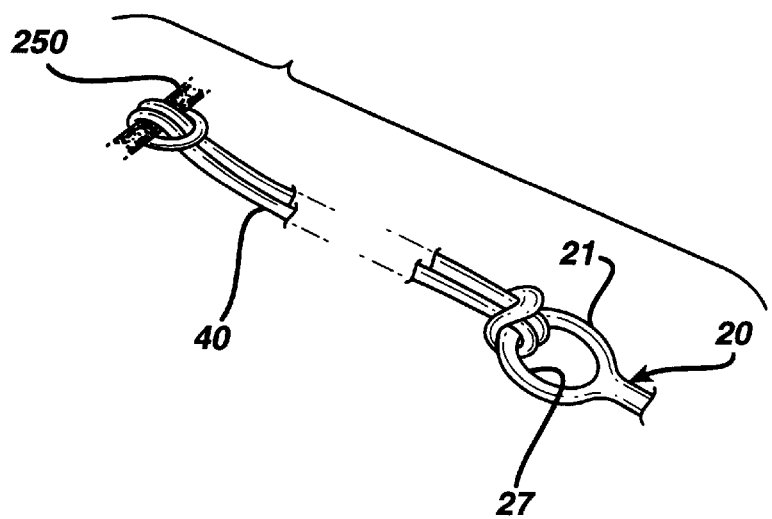
FIG. 11 is a partial, exploded perspective view illustrating the attachment of the elastomeric members to the mesh and engagement members of the mesh-attachment device combinations of FIGS. 5 and 10.
Figure 12A:
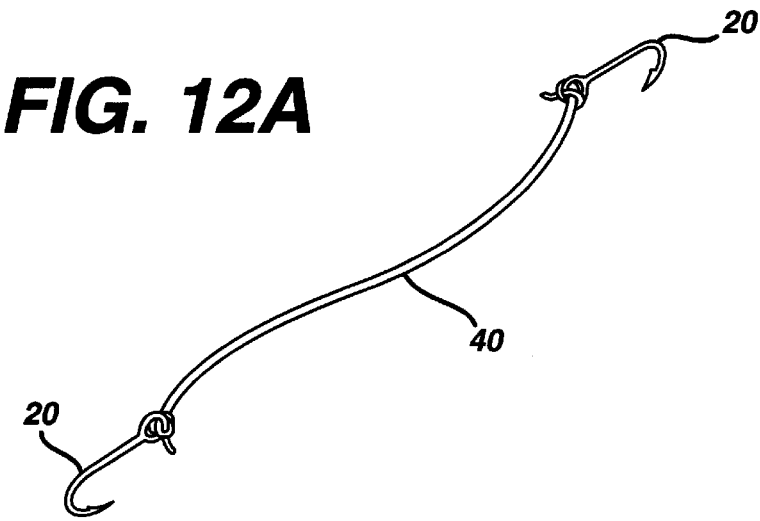
FIG. 12A is a perspective view of an alternate embodiment of the fastening device of the present invention having a single hook mounted to an elastomeric member; the elastomeric member has a rod configuration.
Figure 12B:
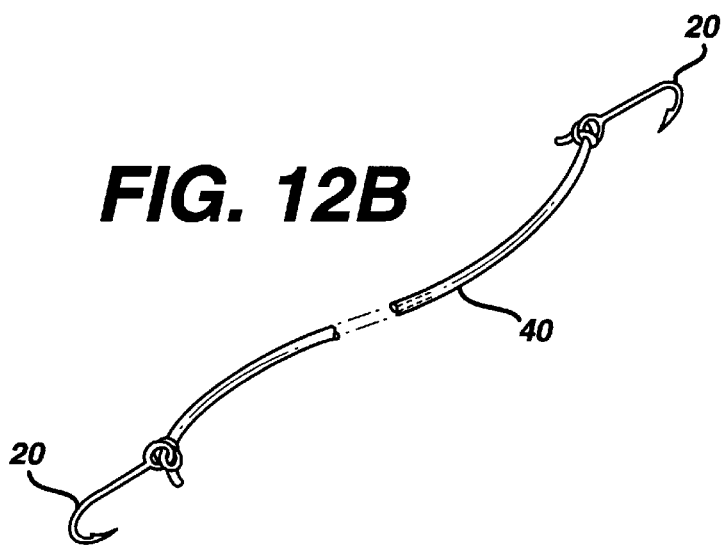
FIG. 12B is a perspective view of an alternate embodiment of the fastening device of the present invention having a single hook mounted to an elastomeric member; the elastomeric member has a tubular configuration.
Figure 12C:
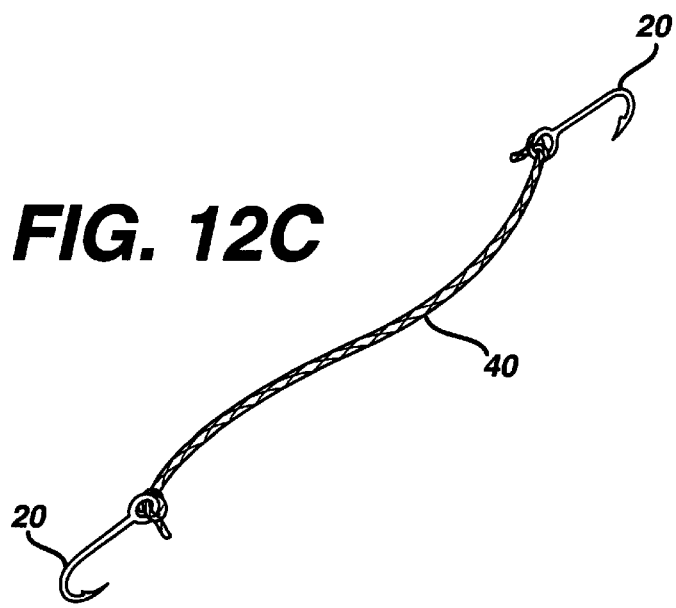
FIG. 12C is a perspective view of an alternate embodiment of the fastening device of the present invention having a single hook mounted to an elastomeric member; the elastomeric member has a multiple filament configuration.

A surgical attachment device 10 of the present invention is illustrated in FIG. 1. The device 10 is seen to have elastomeric member 40 and tissue engagement hook member 20. Elastomeric member 40 may be in the form of an endless band (e.g., a belt) or may have a configuration such as a unitary member, e.g., a flat rectangular strap. Elastomeric member 40 may have any shape or configuration sufficient to effectively provide tension when stretched from its resting state. The shapes include but are not limited to monofilaments, multiple filaments, bands, belts, braids, thin films, hollow tubes, bars, cylinders, rods, and the like, either singly or in multiples, and combinations and equivalents thereof. It is particularly preferred that the member 40 have a band configuration wherein the member 40 is in the form of an endless belt-type member. Referring to FIGS. 1, 3, 4, 5, 10, and 11, the member 40 is seen to have an endless band configuration. Member 40 is seen to have a strap configuration in FIG. 2. As seen in FIGS. 12A–C, the member is seen to have, respectively, a rod configuration, a tube configuration, and a multiple filament configuration. It is preferred, when the member 40 has a rod configuration as in FIG. 12A, that a monofilament surgical suture having the requisite properties is used. Similarly, when member 40 has a multiple filament configuration as in FIG. 12C, it is also preferred that a surgical suture having the requisite properties is used.

Figure 2:
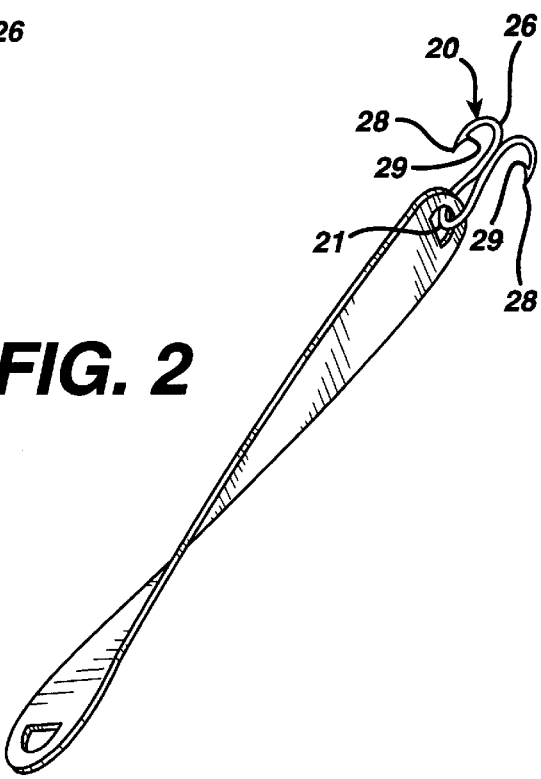
FIG. 2 is a perspective view of an alternate embodiment of the attachment device of the present invention having a double hooks mounted to the elastomeric member; the elastomeric member has a strap configuration.
Figure 3:
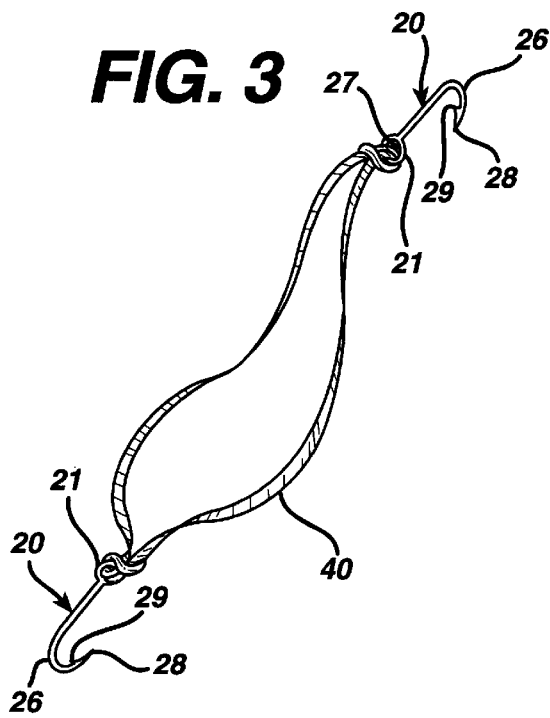
FIG. 3 is a perspective view of an alternate embodiment of the tissue attachment device of the present invention illustrating two separate hooks mounted to an elastomeric member.
Figure 4:
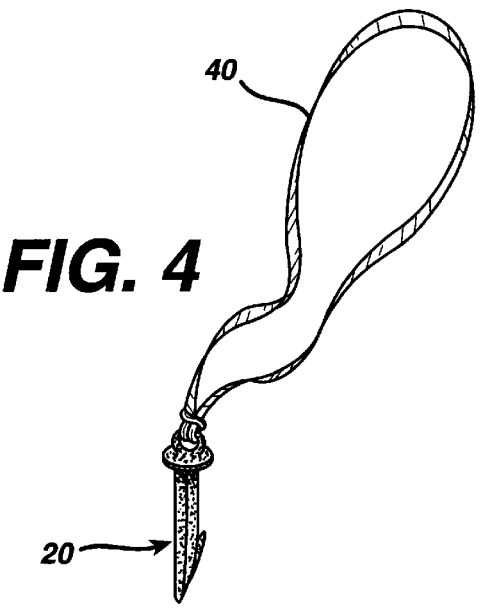
FIG. 4 is a perspective view of an alternate embodiment of the tissue attachment device of the present invention illustrating a surgical tack mounted to an elastomeric member.
Figure 6:
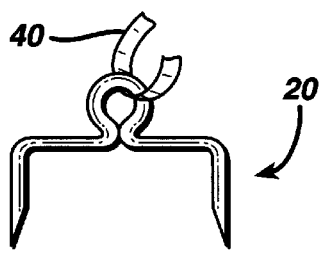
FIG. 6 is an alternate embodiment of the attachment device of the present invention wherein the elastomeric member is mounted to a surgical staple.
Figure 7:
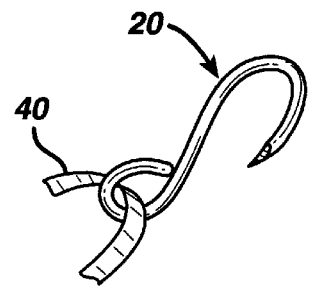
FIG. 7 is an alternate embodiment of the attachment device of the present invention wherein the elastomeric member is mounted to an S-shaped member.

The tissue engagement member 20 is seen to have a preferred hook-like configuration (see FIGS. 1–3). The tissue engagement member 20 is seen to have a proximal end 21 and a distal end 26. Piercing point 28 is seen to extend from the distal end 26. Piercing point 28 may have any conventional tissue piercing configuration, including sharp tapered points and blunt tips. Optionally, piercing point 28 has locking barb 29 to fix or lock the engagement member 20 in tissue. If desired, more than one hook may be mounted together to form member 20 as seen in FIG. 2. The engagement member 20 will preferably have a proximal structure for mounting member 40 such as the opening 27 in end 21, although such a structure is not required. Other equivalent mounting methods may be used including adhesives, mechanical fasteners and the like. Other embodiments of the tissue engagement member 20 include a staple as seen in FIG. 6, an S-hook as seen in FIG. 7 and a surgical tack having an optional barb as seen in FIG. 4.

The elastomeric member 40 may be made from conventional elastomeric, biocompatible, bio-absorbable polymers having sufficient elasticity to effectively apply a tensile force when elongated. The following elastomeric material is particularly preferred: caprolactone/polyglycolide 45/55 and caprolactone/polyglycolide 40/60. The elastomeric materials will preferably have the following characteristics: an elastic strain of about 10% to about 25%, a modulus of about 500 psi to about 10,000 psi, and a plastic strain of about 100% to about 1,000%. The elastomeric member 40 may also be made from conventional biocompatible, absorbable materials such as caprolactone, polydioxanone, polylactide, glycolide, trimethylcarbonate and blends thereof and the like. In addition, elastomeric member 40 may be made from conventional, biocompatible, nonabsorbable elastomeric materials such as silicone, natural rubber, latex, fluoroelastomers, thermoplastic elastomer, and the like. The elastomeric member 40 may also be made from absorbable polymer compositions such as those disclosed in commonly assigned co-pending U.S. patent application Ser. No. 08/007,316 filed on Jan. 21, 1993 which is incorporated by reference including random copolymers of ε-caprolactone, trimethylene carbonate, ether lactone, or mixtures thereof, and glycolide, paradioxanone, or mixtures thereof.

The tissue engagement members 20 of the present invention may be made from either conventional bioabsorbable materials or conventional non-absorbable materials, combinations thereof and equivalents thereof. Examples of absorbable materials include homopolymers and copolymers of lactide, glycolide, trimethylene carbonate, caprolactone, and p-dioxanone and blends thereof. Of particular utility are the following two blends:

(1) the blend of poly(p-dioxanone) and a lactide/glycolide copolymer, as disclosed in U.S. Pat. No. 4,646,741 which is incorporated by reference;

(2) the glycolide-rich blend of two or more polymers, one polymer being a high lactide content polymer, and the other being a high glycolide content disclosed in U.S. Pat. No. 4,889,119 which is incorporated by reference; and, (3) polyglycolic acid homopolymer and polyglycolide.

The engagement members 20 may also be made from conventional non-absorbable, biocompatible materials including stainless steel, titanium, polymers, composites and the like and equivalents thereof.

As mentioned previously, the tissue engagement member 20 may have additional shapes and configurations in addition to a hook-shaped configuration. The shapes and configurations will include those of conventional tissue fasteners and equivalents thereof having sufficient tissue holding capability to effectively be maintained in tissue when subjected to a pullout force or tensile force applied by the elastomeric member 40. Referring to FIG. 6, member 20 may have a conventional staple configuration. Other configurations include a hook and loop, a surgical tack (see FIG. 4), a plurality of hooks, e.g., a double hook as seen in FIG. 2, a loop, and an S-hook as seen in FIG. 7, and the like and equivalents thereof.

Figure 8:
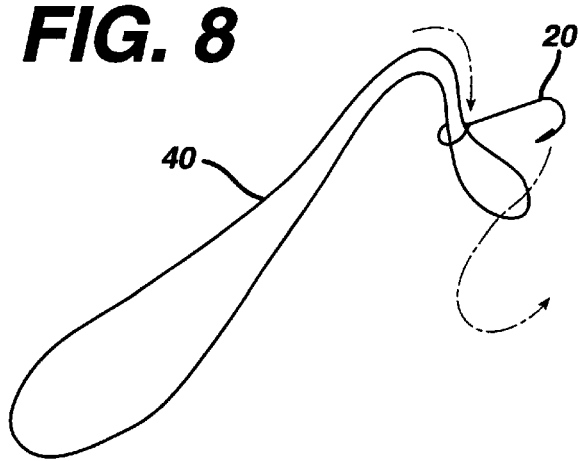
FIGS. 8–9 are perspective views of a preferred method of mounting the elastomeric member to the tissue engagement member.
Figure 9:
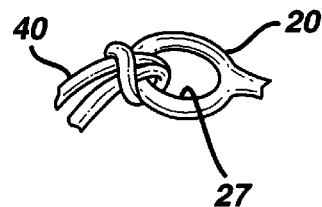

The tissue engagement member 20 will typically be attached to the elastomeric member 40 using conventional techniques including knots, wraps, slip fits, mechanical fasteners, insert molding or co-molding, and the like. A particularly preferred method of attachment as seen in FIGS. 8, 9 and 11 is to throw a continuous loop of elastomeric member 40 through an opening 27 in the tissue engagement member 20 and then back through the continuous member 40 to provide a cinch. Typically, one engagement member will 20 will be mounted to one end of the elastomeric member 40, however, in the practice of the present invention one or more engagement members 20 may be mounted to each end of member 40 and even along the sides thereof if so desired as illustrated in FIG. 3.

Figure 5:
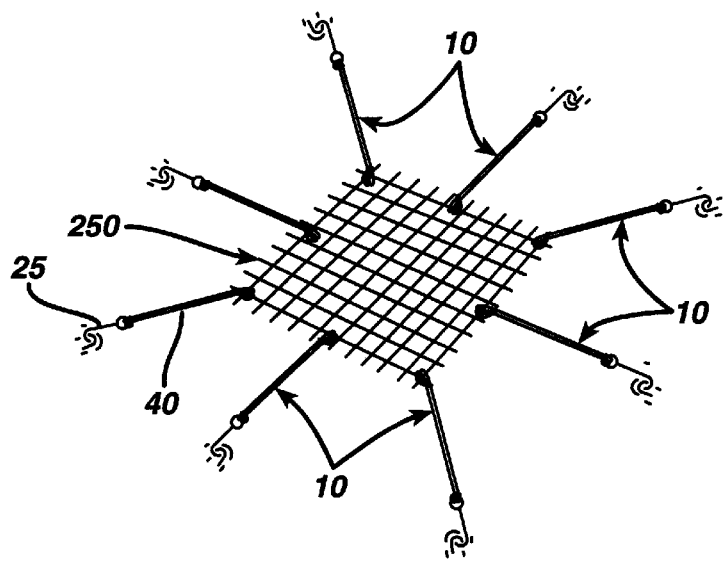
FIG. 5 is a perspective view of the combination of a plurality of attachment devices of the present invention mounted to a surgical mesh.

The surgical meshes 250 (See FIGS. 5 and 10) which can be used in the practice of the present invention include conventional commercially available meshes and equivalents thereof including: Prolene® (polypropylene), Merselene® (polyester), Kissin® (Polydioxanone-Vicryl® blend non-woven), Goretex® (Teflon®) and Vicryl® (lactide-glycolide copolymer). The surgical meshes may be made from absorbable or non-absorbable materials. The absorbable materials may include polydioxanone, glycolide, lactide and caprolactone. Nonabsorbable materials may include polypropylene, PTFE, and polyester. The surgical meshes 250 may be used with the fasteners 10 of the present invention to secure the mesh 250 to tissue as seen in FIGS. 5 and 10. Typically a plurality of fasteners 10 mounted about the periphery of the mesh will be utilized. A sufficient number of fasteners 10 will be used to effectively secure the mesh 250 to tissue. The fasteners 10 can be mounted to the mesh 250 by the manufacturer, of they can be mounted during the surgical procedure by the surgeon.

The following example is illustrative of the principles and practice of the present invention, although not limited thereto.

EXAMPLE I

A patient is prepared for surgery using conventional surgical preparatory techniques. The patient is anesthetized with a sufficient dose of a conventional anaesthesia to induce an effective anaesthetized state. An incision is made into the patient's abdominal cavity in order to access the site of an inguinal hernia using conventional surgical techniques. After the site of the inguinal hernia is prepared using conventional surgical techniques, a piece of a conventional, biocompatible surgical mesh 250 is placed over the site of the inguinal hernia. The attachment devices 10 of the present invention are previously mounted to the mesh 250 by applying cinch knots as seen in FIGS. 8, 9 and 11.

Absorbable attachment devices 10 of the present invention are applied in the following manner (see FIG. 10). Tension is applied to an attachment device 10 while keeping the mesh 250 in place, thereby stretching member 40, and a tissue engagement member 20 having a hook configuration is secured to nearby tissue. Another device 10 is attached in the same manner to an opposite side of the mesh 250. The remaining devices 10 are attached in an alternating radial fashion in a pattern similar to the pattern used to tighten bolts on a tire or pipe flange.

After the mesh 250 is secured by using a sufficient number of attachment devices 10 to effectively affix the mesh, for example about 8–10, the inguinal hernia procedure is completed in a conventional manner and the incision in the wall of the abdominal cavity is closed using conventional surgical sutures. The devices 10 maintain the surgical mesh 250 over the site of the inguinal hernia (See FIG. 10) and are absorbed by the patient's body over time.

The attachment devices 10 of the present invention have several advantages. The devices 10 easily conform to body contours. The devices 10 are easy for the surgeon to apply. The devices 10 may be used to secure tissue to tissue, suspend organs, or secure surgical meshes to tissue. The devices 10 when emplaced may apply a variable amount of tensile force in relation to the degree of elongation of the elastic member 40 when emplaced. The devices 10 may be made of absorbable compositions and can thereby gradually absorb in the body over time.

Although this invention has been shown and described with respect to detailed embodiments thereof, it will be understood by those skilled in the art that various changes in form and detail thereof may be made without departing from the spirit and scope of the claimed invention.

I claim:

1. A bioabsorbable surgical attachment device for attaching tissue, comprising:

a bioabsorbable elastomeric member; and, at least one bioabsorbable tissue engagement means mounted to the elastomeric member, wherein the attachment device provides tensioned fastening of tissue.

2. The attachment device of claim 1 wherein the tissue engagement means comprises at least one hook, said hook having a distal end and a proximal end.

3. The attachment device of claim 2 additionally comprising a piercing point extending from the distal end of each hook.

4. The attachment device of claim 3 wherein the piercing point comprises a blunt tip.

5. The attachment device of claim 2 further comprising means for locking the hook in tissue.

6. The attachment device of claim 1 wherein the tissue engagement means comprises a surgical tack.

7. The attachment device of claim 1 wherein the tissue engagement means comprises a surgical staple.

8. The attachment device of claim 1 wherein the elastomeric member comprises an endless belt.

9. The attachment device of claim 1 wherein the elastomeric member comprises a flat rectangular band.

10. The attachment device of claim 1 wherein the elastomeric member comprises a rod.

11. The attachment device of claim 1 wherein the elastomeric member comprises a tube.

12. The attachment device of claim 1 wherein the elastomeric member comprises multiple filaments.

13. The attachment device of claim 1 wherein the elastomeric member comprises a surgical suture.

14. A method of securing tissue under tensioned fastening, comprising:

mounting a bioabsorbable surgical attachment device to tissue, the bioabsorbable surgical device comprising a bioabsorbable elastic member, and at least two bioabsorbable tissue engagement means mounted to the elastomeric member, wherein a first bioabsorbable tissue engagement means is mounted to the tissue, then the elastomeric member is stretched and at least one additional bioabsorbable tissue engagement means mounted to the elastomeric member is attached to the tissue such that the engagement means are at least partially implanted in tissue, thereby providing tensioned fastening.

\* \* \* \* \*